United States Patent [19]
Ayer et al.

[11] Patent Number: 4,810,502
[45] Date of Patent: * Mar. 7, 1989

[54] PSEUDOEPHEDRINE BROMPHENIRAMINE THERAPY

[75] Inventors: Atul D. Ayer, Mt. View; Lawrence G. Hamel, Sunnyvale, both of Calif.

[73] Assignee: ALZA Corporation, Palo Alto, Calif.

[*] Notice: The portion of the term of this patent subsequent to May 5, 2004 has been disclaimed.

[21] Appl. No.: 19,989

[22] Filed: Feb. 27, 1987

[51] Int. Cl.⁴ .......................... A61K 9/22; A61K 9/32; A61K 9/36
[52] U.S. Cl. .................................. 424/473; 424/475; 424/480; 604/892.1
[58] Field of Search ...................... 424/473, 475, 480; 604/892.1

[56] References Cited

U.S. PATENT DOCUMENTS

| | | | |
|---|---|---|---|
| 4,309,405 | 1/1982 | Guley et al. | 424/493 |
| 4,369,172 | 1/1982 | Schor et al. | 424/22 |
| 4,449,983 | 5/1984 | Cortese et al. | 604/892 |
| 4,457,907 | 7/1984 | Porter | 424/16 |
| 4,552,899 | 11/1985 | Sunshine et al. | 514/653 |
| 4,576,604 | 3/1986 | Guittard et al. | 604/890 |
| 4,609,374 | 9/1986 | Ayer | 604/892 |
| 4,612,008 | 9/1986 | Wong et al. | 604/891 |
| 4,662,880 | 5/1987 | Hamel et al. | 424/473 |

Primary Examiner—Nancy A. B. Swisher
Attorney, Agent, or Firm—Paul L. Sabatine; Edward L. Mandell; Steven F. Stone

[57] ABSTRACT

A dosage form is disclosed for delivering the beneficial drugs pseudoephedrine and brompheniramine to a biological environment of use.

8 Claims, 1 Drawing Sheet

PSEUDOEPHEDRINE BROMPHENIRAMINE THERAPY

This patent application is copending with U.S. patent application Ser. No. 06/839,384 filed on Mar. 14, 1986, now U.S. Pat. No. 4,662,880 issued May 5, 1988; with U.S. patent application Ser. No. 06/853,109 filed on Apr. 17, 1986, and also copending with a U.S. patent application, U.S. patent application Ser. No. 07/007,879 filed Jan. 28, 1987. This patent application and the copending patent applications all are assigned to the ALZA Corporation of Palo Alto, Calif.

FIELD OF THE INVENTION

This invention pertains to pseudoephedrine and brompheniramine therapy. More particularly, the invention concerns an improvement in means for providing instant pseudoephedrine and brompheniramine to a biological receptor.

BACKGROUND OF THE INVENTION

Antihistamine and decongestants are used for the temporary relief of symptoms of the common cold, allergic rhinitis and sinusitis. The antihistaine brompheniramine and the decongestant pseudoephedrine are therapeutically indicated for patients needing relief of these symptoms.

Brompheniramine is a propylamine derivative antihistamine. Brompheniramine is a racemic mixture of the dextro and levo isomers. Pharmacologic activity is predominantly due to the d-isomer. Dextrobrompheniramine, the dextro isomer, is approximately twice as active. Brompheniramine is administered for its effects as a therapeutically acceptable salt, preferably as brompheniramine maleate. Brompheniramine maleate occurs as a white crystalline powder, freely soluble in aqueous-type fluids, and it is absorbed from the gastrointestinal tract.

Pseudoephedrine is a sympathomimetic drug which occurs naturally in plants of the Ephedra. Pseudoephedrine is a stereoisomer of ephedrine. Pseudoephedrine is administered for its beneficial effects as a therapeutically acceptable salt, preferably as the hydrochloride or the sulfate. Pseudoephedrine hydrochloride occurs as a fine, white crystal or powder; it is very soluble in aqueous-type fluids and it is absorbed from the gastrointestinal tract.

In copending patent application Ser. No. 06/839,384 a presentation is set forth concerning the desirability of providing a pharmaceutical dosage form comprising the two different drugs that are initially delivered in a therapeutically effective amount, followed by delivery of the drugs at a controlled rate, and for a time period, established to meet a specific therapeutic need. That is, as discussed therein, it would be desirable to provide a dosage form that comprises an exterior lamina comprising pseudoephedrine, brompheniramine and a releasable binder, which lamina delivers both drugs immediately for substantially eliminating the start-up time of the dosage form and for providing immediate therapy to a recipient. The exterior drug-containing lamina for delivering an initial drug-pulse act in cooperation with the dosage form that follows with the drugs then delivered at a controlled rate over time.

Additionally, as discussed therein, it would be desirable to provide a pharmaceutical dosage form comprising the two different drugs for their simultaneous administration for obtaining the physiological and the pharmacological benefits of each drug. Such a novel dosage form could be used for the desired medical relief where each individual drug addresses different symptoms of the particular medical situation. Prior to the invention disclosed and claimed in application Ser. No. 06/839,384 the co-administration of these drugs in a predetermined ratio did not appear feasible. For example, prior to that application pseudoephedrine and brompheniramine appeared to be kinetically incompatible in a pharmaceutical osmotically-controlled dosage form for their respective administrations within prescribed ratios because of their individual osmotic properties and their solubilities. Additionally, before the copending application, it was unobvious from their pharmacokinetic properties that pseudoephedrine and brompheniramine could be administered from a dosage form to a warm-blooded animal at rates that are individually selected to achieve each of their separate therapeutic plasma concentrations.

Thus, in the light of the above presentation, it will be appreciated by those skilled in the dispensing art that the novel and unique dosage form disclosed and claimed in the copending application Ser. No. 06/839,384 has made available (1) administering a pulsed amount of pseudoephedrine and brompheniramine and (2) made available a means for housing the pseudoephedrine and the brompheniramine for their administration at a controlled and continuous rate and in therapeutically effective ratio for obtaining the benefits of each drug, has a definite use and also represents a valuable contribution to the dispensing art. Also, it will be appreciated by those versed in the dispensing art that if an improvement is made available in the means for providing a pulsed amount of pseudoephedrine and brompheniramine from the dosage form, the improvement also will have a definite use and represent an additionally valuable contribution to the dispensing art.

OBJECTS OF THE INVENTION

It is an immediate object of this invention to provide an improvement in pseudoephedrine and brompheniramine therapy for administering the drugs to biological receptor sites to produce the desired pharmacokinetic effects.

Another object of the invention is to provide an improvement in a dosage form that can dispense pseudoephedrine and brompheniramine in a preselected ratio and at controlled rates for obtaining the pharmacological and the physiological benefit of each drug, and which dosage form thusly represents an improvement and advancement in therapy.

Another object of the invention is to provide an osmotic system manufactured in the form of an osmotic device that comprises an improvement in an exterior lamina composition comprising pseudoephedrine and brompheniramine and a releasable binder that delivers the drugs immediately for increasing the period of time pseudoephedrine and brompheniramine are available for performing their beneficial effects, followed by prolonged release of the drugs from the interior of the osmotic device.

Another object of the invention is to provide an osmotic system adapted for administering pseudoephedrine and brompheniramine to a warm-blooded animal from a lamina that exhibits a resistance to cracking and prolonged self-stability and comprises pseudoephedrine and brompheniramine for delivering an initial pulse of these drugs in the lamina that acts in cooperation with the osmotic system that follows with delivery of pseudoephedrine and brompheniramine at a rate controlled by the osmotic system.

Another object of the invention is to provide an osmotically controlled dosage form that can house pseudoephedrine and brompheniramine and can codispense the two drugs to their biological drug receptors for their separate therapeutic activities over a prolonged period of time.

Another object of the invention is to provide an improvement in an osmotic device, which osmotic device comprises a single compartment containing a composition comprising a member selected from the group consisting of pseudoephedrine and its therapeutically acceptable salts and brompheniramine and its therapeutically acceptable salts, and which osmotic device can administer simultaneously the pseudoephedrine and the brompheniramine at a preselected prescribed ratio for providing a complete pharmaceutical regimen for the two drugs to a warm-blooded animal.

Another object of the invention is to provide a complete pharmaceutical regimen for a composition comprising a pseudoephedrine and a brompheniramine with the pharmacological parameters of the composition more favorable than those of the drugs alone, and which composition can be dispensed from an osmotic delivery system, the use of which requires intervention only for initiation and possibly termination of the regimen.

Another object of the invention is to provide an osmotic device for dispensing pseudoephedrine and brompheniramine, which osmotic device comprises a wall member whose fluid permeability increases over a prolonged period of time.

Another object of the present invention is to provide an osmotic therapeutic system comprising pseudoephedrine and brompheniramine that are codelivered at a mass ratio concomitantly with the system exhibiting increased permeability that is gradual over time.

Other objects, features and advantages of the invention will be more apparent to those versed in the art from the following specification, taken in conjunction with the drawings and the accompanying claims.

BRIEF DESCRIPTION OF THE DRAWINGS

In the drawing figures, which are not drawn to scale but are set forth to illustrate various embodiments of the invention, the drawing figures are as follows.

In the drawings and in the specification, like parts in related figures are identified by like numbers. The terms appearing earlier in the specification and in the description of the drawings, as well as embodiments thereof, are further described elsewhere in the disclosure.

DETAILED DESCRIPTION OF THE DRAWING FIGURES

Figure 1:
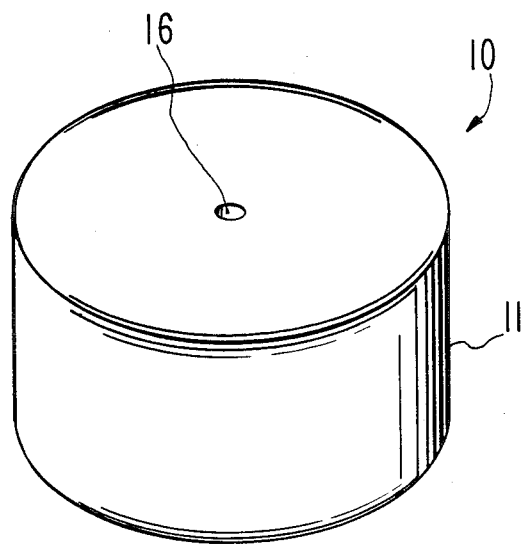
FIG. 1 is a view of an osmotic device designed and shaped for orally administering the two beneficial drugs pseudoephedrine and brompheniramine to the gastrointestinal tract; and, FIG. 2 is an opened view of the osmotic device of FIG. 1 illustrating the structure of the osmotic device.
Figure 2:
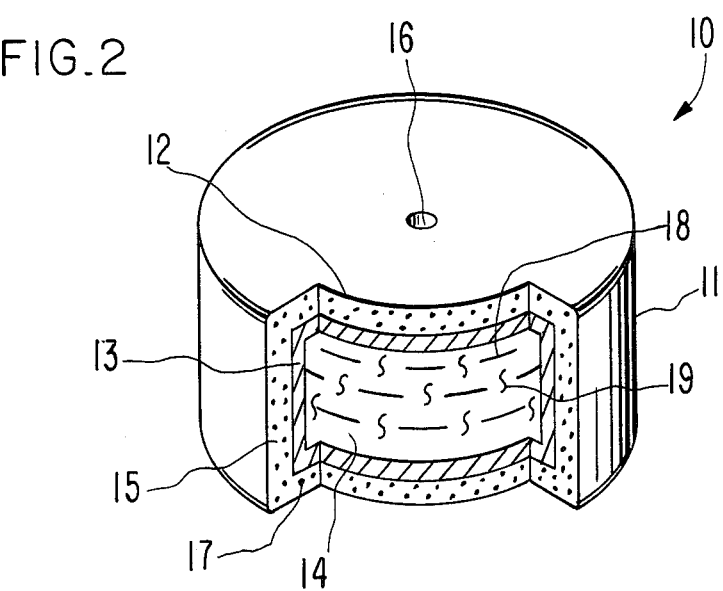

Turning now to the drawing figures in detail, which drawing figures are examples of the dosage form provided by the invention, and which examples are not to be construed as limiting, one example is the osmotic dosage form illustrated in FIG. 1 and FIG. 2 and designated by the numeral 10. In FIG. 1, osmotic dosage form 10 comprises body member 11 that surrounds and forms an internal compartment not seen in FIG. 1.

In FIG. 2, osmotic dosage form 10 is seen in opened view for illustrating the internal structure of dosage form 10. Dosage form 10 comprises body 11 sectioned at 12. Dosage form 10 comprises wall 13 that surrounds and defines an internal compartment 14. An exterior lamina 15 is initially supported on at least a part or all of the exterior surface of wall 13. Wall 13 comprises at least one exit port 16, or more than one exit port means for dispensing the contents of compartment 14 from dosage form 10.

Wall 13 of dosage form 10 comprises a composition that is permeable to the passage of an exterior fluid present in the environment of use, and it is substantially impermeable to the passage of drug and other ingredients present in compartment 14. That is, wall 13 is a semipermeable wall. Semipermeable wall 13 of dosage form 10 is substantially inert, and it maintains its physical and chemical integrity during the drug dispensing life of dosage form 10. The phrase "keeps its physical and chemical integrity" means wall 13 does not lose its structure and it does not change during the dispensing life of dosage form 10. In a presently preferred embodiment wall 13 is formed of a composition comprising cellulose acylate such as cellulose triacetate and hydroxypropyl cellulose. Wall 13 comprises a composition containing from 70 to 85 weight percent (wt %) cellulose triacetate, and from 15 to 30 weight percent hydroxypropylcellulose, with the total weight percent equal to 100. Wall 13, in one presently preferred embodiment, comprises 75 weight percent cellulose triacetate and 25 weight percent hydroxypropylcellulose. In another preferred embodiment wall 13 comprises 80 weight percent cellulose triacetate and 20 weight percent hydroxypropylcellulose. The acetyl content of the cellulose triacetate can be from 39.8% to 43.5%. Wall 13 exhibits an increased permeability to the passage of fluid over time attributed to the presence of hydroxypropylcellulose in wall 13. This unique property of wall 13, acting in cooperation with dosage form 10, enables dosage form 10 to delivery greater than 90% to 95% of its drug content over a prolonged period of 24 hours.

Dosage form 10, manufactured in the form of an osmotic device, comprises an improved lamina 15 coated onto the exterior surface of wall 13. Lamina 15 comprises a composition 17, represented by dots, which composition comprises the beneficial drugs pseudoephedrine and brompheniramine, at least one aqueous erodible nontoxic carrier selected from the group consisting of hydroxypropylmethylcellulose and hydroxypropylcellulose, and at least one member selected from the group consisting of polyethylene oxide and carboxyvinyl polymer. Lamina 15 optionally can comprise a binder and/or a disintegrating agent. Lamina 15 comprising composition 17 is provided for making available instantly the drugs pseudoephedrine and brompheniramine, preferably as their pharmaceutically acceptable salt, to the biological environment of use. In operation when dosage form 10 is in a fluid environment of use exterior lamina 15 disintegrates, dissolves or undergoes dissolution and concurrently delivers composition 17 comprising pseudoephedrine and brompheniramine to a drug receptor. Lamina 15, comprising drug composition 17, by providing immediate drug delivery essentially overcomes the time required for the drugs to be delivered from compartment 14 of dosage form 10. A start-up time is needed for imbibing fluid through semipermeable wall 12 for dosage form 10 to hydrodynamically dispense the components of compartment 14 through exit passageway 16 to the environment of use.

Lamina 15, in one presently preferred embodiment, comprises a composition comprising from 10 to 35 weight percent of a member selected from the group consisting of pseudoephedrine and its therapeutically acceptable addition salt, from 0.5 to 5 wt % of a member selected from the group consisting of brompheniramine and its therapeutically acceptable salts, from 10 to 30 wt % of a least one member selected from the group consisting of polyethylene oxide and carboxyvinyl polymer, from 30 to 55 wt % of hydroxypropylcellulose, from 2 to 10 wt % hydroxypropylmethylcellulose, and other lamina forming ingredients up to 100 wt %. Lamina 15, in one presently preferred embodiment, expressed in milligrams (mg) has 55 to 65 mg of pseudoephedrine, 3 to 8 mg of brompheniramine, 35 to 50 mg of polyethylene oxide; 82 to 92 mg of hydroxypropylcellulose, 3 to 10 mg of hydroxypropylmethylcellulose and other optional lamina forming members; or lamina 15 comprises 55 to 65 mg of pseudoephedrine, 3 to 8 mg of brompheniramine, 35 to 50 mg of carboxyvinyl polymer, 82 to 92 mg of hydroxypropylcellulose, 3 to 10 mg of hydroxypropylmethylcellulose; and other optional lamina 15 forming ingredients. In another preferred embodiment lamina 15 comprises 25 to 35 mg of pseudoephedrine, 1 to 5 mg of brompheniramine, 15 to 30 mg of polyethylene oxide, 30 to 50 mg of hydroxypropylcellulose, 1 to [mg of hydroxypropylmethylcellulose and other optional lamina 15 forming members; or 25 to 35 mg of pseudoephedrine, 1 to 5 mg of brompheniramine, 15 to 30 mg of carboxyvinyl polymer, 30 to 50 mg of hydroxypropylcellulose, 1 to 8 mg of hydroxypropylmethylcellulsoe, and other optional lamina 15 forming ingredients.

More specifically lamina 15, in one embodiment, comprises 60 mg of pseudoephedrine hydrochloride, 4 mg of brompheniramine maleate, 38 mg of polyethylene oxide, 87 mg of hydroxypropylcellulose, 10 mg of hydroxypropylmethylcellulose and 1 mg of magnesium stearate; lamina 15 comprises 60 mg of pseudoephedrine hydrochloride, 4 mg of brompheniramine maleate, 38 mg of carboxyvinyl polymer, 87 mg of hydroxypropylcellulose, 10 mg of hydroxypropylmethylcellulose, and 1 mg of magnesium stearate. Other specific embodiments provided by the invention comprising lamina 15 have 30 mg of pseudoephedrine hydrochloride, 3 mg of brompheniramine maleate, 19 mg of polyethylene oxide, 43 mg of hydroxypropylcellulose, 5 mg of hydroxypropylmethylcellulose, and 0.5 mg of magnesium stearate; a lamina comprising 30 mg of pseudoephedrine hydrochloride, 6 mg of brompheniramine maleate, 19 mg of carboxyvinyl polymer, 40 mg of hydroxypropylcellulose, 8.5 mg of hydroxypropylmethylcellulose, and 0.5 mg of magnesium stearate, and the like. Lamina 15 begins to release the beneficial drug pair instantly in the fluid environment of use, and it completely releases all of the drug pair during the first 30 to 40 minutes. This instant release thereby provides the drug pair for immediate passage into the plasma of a recipient.

In lamina 15 the improvement comprises employing a polymer that embraces both viscous and elastic properties, exhibits thermoplastic behavior, makes the lamina forming composition spread evenly for better adhesion to semipermeable wall 13. In lamina 15 the improvement comprises using a polyethylene oxide or a carboxyvinyl polymer for the stated purpose. The polyethylene oxide polymer operable for the present purpose comprise a poly(alkylene oxide) polymer of the general formula $(O-R)_m$, wherein R is a straight or a branched chain alkylene group, and m is from 50 to 150,000 as exemplified by poly(ethylene oxide) of the general formula $(O-CH_2CH_2)_m$ having a molecular weight of from 10,000 to 5,000,000; and, the carboxyvinyl polymer is a carboxyvinylpolymethylene polymer, a polymer formed in one embodiment by cross-linking acrylic acid with a polyallyl ether of sucrose and which generic carboxyvinyl polymer as embodied herein has a molecular weight of 5,000 to 400,000. The use of these polymers also increases the shelf life of the dosage form and lessens the incidence of cracking of the lamina. The hydroxypropylcellulose used for lamina 15 comprises hydroxylpropyl content of 7% to 16%; and, the hydroxy propylmethylcellulose used for the purpose of this invention exhibits a number average molecular weight of from 5,000 to 150,000. Lamina 15 optionally can comprise other ingredients exemplified by lubricants such as magnesium stearate, stearic acid and the like; disintegrating agents such as starch, cross-linked polyvinyl pyrrolidone and the like; binders such as noncross-linked polyvinyl pyrrolidone, and the like.

Internal compartment 14 houses a dispensable composition comprising the beneficial drugs pseudoephedrine 18, identified by dashes, and beneficial drug brompheniramine 19, identified by wavy lines. The two drugs are present in compartment 14 in a fixed ratio and they are dispensed at a rate of release essentially equal to the ratios at which drug 18 and drug 19 were formulated into compartment 14. The release rate ratio, essentially equal to their compartment ratio, is both unobvious and unexpected based on thermodynamic physics. Thermodynamics indicates the two drugs would be released at their equilibrium solubility ratios; for example, in an embodiment comprising pseudoephedrine hydrochloride and brompheniramine maleate at a ratio of 1.75:1. While dosage form 10 in operation codelivered pseudoephedrine hydrochloride and brompheniramine maleate at their mass ratio of 15:1. This release rate ratio is the same ratio as the two drugs were formulated into compartment 14. According to thermodynamic equilibrium equations applicable to an osmotic dosage form for codelivering pseudoephedrine hydrochloride, identified as drug A, and brompheniramine maleate, identified as drug B, the equations are as follows:

$$S_T = S_A + S_B \tag{1}$$

wherein $S_T$ is the total solubility of drug A and drug B in fluid imbibed into compartment 14; $S_A$ is the solubility of drug A in the fluid and $S_B$ is the solubility of drug B in the fluid; the release rate $RR_A$ for drug A is given by equation (2):

$$RR_A = \frac{k}{h} A \Delta \pi S_A \tag{2}$$

wherein $S_A$ is the solubility of drug A in fluid in the compartment, k is the permeability of semipermeable wall 13 to aqueous-type fluids present in the environment of use, h is the thickness of wall 13, $\Delta \pi$ is the total osmotic pressure gradient of the drug formulation across wall 13 against an exterior fluid present in the environment of use, and A is the area of wall 13; and by equation (3) for the controlled release rate $RR_B$ for drug B as follows:

$$RR_B = \frac{k}{h} A\Delta\pi S_B \qquad (3)$$

wherein $S_B$ is the solubility of drug B in the presence of fluid imbibed through wall 13 into compartment 14, k is the permeability of wall 13 to the fluid present in the environment, h is the thickness of wall 13, $\Delta\pi$ is the total osmotic pressure gradient of the drug formulation across wall 13 against fluid present in the environment of use, and A is the area of wall 13; then, combining equations (2) and (3) the equilibrium solubility ratio SR for drug A exemplified by pseudoephedrine hydrochloride and for drug B exemplified by brompheniramine maleate is given by equations (4) and (5):

$$\frac{RR_A}{RR_B} = \frac{S_A}{S_B} = \frac{572 \text{ mg/ml}}{327 \text{ mg/ml}} \qquad (4)$$

$$SR = 1.75:1 \qquad (5)$$

Instead, the release rate ratios provided by this invention for drug A and drug B is given by equation (6) as follows:

$$\frac{RR_A}{RR_B} = \frac{C_A}{C_B} \qquad (6)$$

wherein $C_A$ is the concentration of drug A in compartment 16 at the initiation of the drug dispensing period, and $C_B$ is the concentration of drug B at the beginning of the drug dispensing period, the (7):

$$\frac{RR_A}{RR_B} = \frac{120}{8} \qquad (7)$$

$$RR_{A-B} = 15:1$$

which two drugs, as determined by scientific measurements, were co-released in essentially the same ratio as their initial charge in compartment 14 at time zero. The ratio of the two drugs inside the compartment can be selected according to their therapeutic need. In this preselection, the controlled release rate for the codelivered drugs comprise essentially the same ratio as their mass ratio in the compartment. Generally in one osmotic dosage form provided by the invention the compartment contains from 170 to 200 mg of pseudoephedrine and from 10 to 20 mg of brompheniramine, with more specific dosages comprising (a) 180 mg of pseudoephedrine hydrochloride and 18 mg of brompheniramine maleate; and (b) 180 mg of pseudoephedrine hydrochloride and 10 mg of brompheniramine maleate. In another osmotic dosage form provided by the invention, the compartment contains from 80 to 110 mg of pseudoephedrine and 3 to 8 mg of brompheniramine, with more specific dosage forms comprising (c) 90 mg of pseudoephedrine hydrochloride and 5 mg of brompheniramine maleate; and (d) 90 mg of pseudoephedrine hydrochloride and 3 mg of brompheniramine maleate. The preferred mass ratio is from 8:1 to 20:1 with a more specific mass ratio comprising 10:1 to 15:1 expressed as pseudoephedrine to brompheniramine. The compartment can contain also from 20 to 30 mg of sodium chloride, usually about 25 mg in a dosage form. The sodium chloride aids in codispensing a higher percent of the drugs delivered at zero-order, usually 15 hours and longer. The compartment can contain also hydroxypropylmethylcellulose as an aid for controlling the dissolution of the composition in the compartment.

The expression "exit means" as used herein comprises means and methods suitable for co-releasing the beneficial drugs pseudoephedrine and brompheniramine from the dispensing device. The means include at least one passageway or orifice that passes through wall 13 for communicating with the drugs in compartment 14. The expression "at least one passageway" includes aperture, orifice, bore, pore, porous element through which drugs can migrate, a hollow fiber, capillary tube, and the like. The expression includes also a material that erodes or is leached from wall 13 in the fluid environment of use to produce at least one passageway in the device. Representative materials suitable for forming at least one passageway, or a multiplicity of passageways, include an erodible poly(glycolic) or poly(lactic) acid member in the wall, a gelatinous filament, poly(vinyl alcohol), leachable materials such as fluid removable pore forming polysaccharides, salts, or oxides and the like. A passageway or a plurality of passageways can be formed by leaching a material such as sorbitol from the wall. The passageway can have any shape, such as round, triangular, square, elliptical, irregular and the like. The device can be constructed with one or more passageways in spaced apart relation on more than a single surface of a dosage form. Passageways and equipment for forming passageways are disclosed in U.S. Pat. Nos. 3,916,899; 4,063,064 and 4,088,864. Passageways formed by leaching are disclosed in U.S. Pat. No. 4,200,098.

The dosage forms of the invention are manufactured by standard manufacturing techniques. For example, in one manufacture the compartment forming ingredients are formulated by the wet granulation technique using an organic cosolvent, such as isopropyl alcoholmethylene dichloride, 80/20 v/v (volume/volume) as the granulating fluid. The ingredients forming the compartment in this manufacture comprising pseudoephedrine hydrochloride, brompheniramine maleate, sodium chloride, hydroxypropylmethylcellulose, and microcrystalline cellulose, are individually passed through a 40 mesh screen and then thoroughly bleded in a mixer. Next, poly(vinylpyrrolidone) is dissolved in a portion of the granulation fluid, the cosolvent described immediately above. Then the poly(vinylpyrrolidone) solution is added slowly to the dry powder blend withccontinual mixing in the blender. The granulating fluid is added until a wet blend is achieved, generally about 400 cc of granulating fluid per kilogram of blend. The wet mass blend is then forced through a 20 mesh screen onto oven trays and dried for 18 to 24 hours at 50° C. The dried granules are then sized with a 20 mesh screen. Next magnesium stearate and silicon dioxide are added to the dry, screened granular blend and this blend passed through an 80 mesh screen. The granulation is then put into milling jars and mixed on a jar mill for 10 to 15 minutes.

In another manufacturing process the drugs pseudoephedrine and brompheniramine and other ingredients are blended in a fluid bed granulation. After the powders are dry blended a granulation fluid comprising a solution of poly(vinylpyrrolidone) in water is sprayed onto the powders and dried in the granulator. This process granulates all of the ingredients together while adding the granulation solution. After the granules are dried, the lubricant magnesium stearate is added to the granulation.

The composition forming blend, in either of the above manufacturing processes, is then tabletted using a 35-station Manesty® tablet press. The speed of the press is set at 30 rpm and the maximum load set a 2 tons. Two dosage forms are tabletted using the press, one using a 7/32 inch (5.55 mm) round, standard concave punch, and the other using a 3/16 inch (4.76 mm) round, standard concave punch.

The semipermeable wall of the osmotic dosage systems can be formed in one other technique comprising using the air suspension procedure. This procedure consists in suspending and tumbling the drug compressed core forming compartment in a current of air and a wall forming solution comprising cellulose acetate and hydroxypropyl cellulose and a solution such as methylene chloride and methanol until the wall is applied to the drug forming compartment. The air suspension procedure is well suited for independently forming the wall. The air suspension procedure is described in U.S. Pat. No. 2,799,241; in J. Am. Pharm. Assoc., Vol 48, pp 451–459, 1959; and ibid. Vol 49, pp 82–84, 1960.

The osmoic dosage form also can be coated with the wall forming composition with a Wurster® air suspension coater, using a methylene dichloride/methanol cosolvent 80/20 v/v, using 2.5% to 4% solids. The Aeromatic® air suspension coater using a methylene dichloride/methanol cosolvent 87/13 v/v also can be used for applying the wall. Other wall forming techniques such as pan coating can be used for prvviding the dosage form. In the pan coating system, wall forming composition is deposited by successive spraying of the composition on the drug, accompanied by tumbling in a rotating pan. An exit port is drilled through the semipermeable wall and the systems are dried for removing the solvent. The exterior drug, quick-releasing lamina comprising the drugs pseudoephedrine and bromphen-iramine, and other lamina forming ingredients comprising hydroxypropylcellulose, polyethylene oxide, and a portion of hydroxypropylmethylcellulose are added to a fluid bed granulator and the materials blended in a moving current of air. In a separate reactor a portion of hydroxypropylmethylcellulose is added to distilled water. Then, the granulating fluids sprayed onto the fluidizing powders until all the solution is used and the powders are granular. The fluidizing process is continued until the granulation is dry. Next, the lubricant magnesium stearate is added to the granules and the blending continued for a few minutes. The immediate release lamina is compressed around the compartment from drugs prepared above. Finally, if needed, the lamina wall coated compartments are dried to yield the final dosage forms. Generally the semipermeable wall formed by these techniques will have a thickness of 2 to 20 mils, with a presently preferred thickness of 4 to 10 mils. The exterior lamina generally will have a thickness of 5 to 150 mils, usually 5 to 75 mils.

Exemplary solvents suitable for manufacturing the wall or the lamina include inert inorganic and organic solvents that do not adversely harm the wall, the lamina and the final systems. The solvents broadly include members selected from the group consisting of alcohols, ketones, esters, ethers, aliphatic hydrocarbons, halogenated solvents, cycloaliphatic solvents, aromatic, heterocyclic, aqueous solvents and mixtures thereof.

Following the procedures of the invention a dosage form is prepared as follows: 67.45 kgs of pseudoephedrine hydrochloride, 4.50 kg of brompheniramine maleate, 9.55 kgs of sodium chloride, 3.0 kgs of hydroxypropylmethylcellulose, and 10.0 kgs of microcrystalline cellulose are blended in a granulator using a moving stream of air. Next, in a separate blender 5.0 kg of polyvinylpyrrolidone is blended with 57.5 kgs of distilled water to yield a granulation solution. Next the granulation solution is sprayed onto the previously prepared fluidized powders until all of the granulation fluid is used and the powders are granular. The fluidizing is continued until the granulation is dry. Then, 0.50 kg of magnesium stearate is added to the granules and all the ingredients blended for about 7 minutes. Then, the granulation is compressed into dosage forming cores having a diameter of 7/32 inches, or 5.56 mm.

Next, a semipermeable wall forming composition comprising 75 wt % of cellulose triacetate having an acetyl content of 43.5%, and 25 wt % hydroxypropylcellulose is prepared as follows: first, to a blending vessel is added 76 parts of methylene chloride and 24 parts of methanol and slowly to the solvent mixture is added 15 kgs of the semipermeable wall forming composition and all the ingredients stirred until a clear wall forming solution results. The wall forming solution contained 3.5% solids. Next, a plurality of dosage forming cores are surrounded with the wall forming composition in a pan coater. The wall forming process is continued until a wall weighing about 11 mgs is coated around each core. Then, the semipermeable wall coated drug cores are dried and at least one exit passageway is laser drilled through the wall. The passageway connects the exterior of the dosage form with the compartment. The passageways have a diameter of about 0.20 mm to 0.60 mm.

Next, the drug releasing exterior lamina is prepared from a batch composition comprising 75.0 kgs of pseudoephedrine hydrochloride, 5.0 kgs of brompheniramine maleate, 108.8 kgs of hydroxypropylcellulose, 47.5 kgs of polyethylene oxide and 6.25 kgs of hydroxypropylmethylcellulose as follows: first, the following ingredients are added to the fluid bed granulator: pseudoephedrine hydrochloride, brompheniramine maleate, hydroxypropylcellulose, polyethylene oxide having a molecular weight of about 100,000 and hydroxypropylmethylcellulose, and all the ingredients blended using an air stream. Next, in a separate container 6.25 kgs of hydroxypropylmethylcellulose is blended with 98 kgs of distilled water to yield a granulation fluid comprising 6% solids. The freshly prepared granulating fluid is sprayed onto the fluidized powders until all the granulating fluid is used and the powders are granular. The fluidizing is continued until the granulation is dry. Then, 1.25 kgs of magnesium stearate is added to the granules and the blending continued for about 8 to 9 minutes. Finally, the drug containing lamina is pressed around the exterior surface of the semipermeable wall of the dosage form. The dosage form provided by this manufacture comprised in the compartment 60 mg of pseudoephedrine hydrochloride, 4 mg of brompheniramine maleate, 8.49 mg of sodium chloride, 2.67 mg of hydroxypropylmethylcellulose, 8.89 mg of microcrystalline cellulose, 4.45 mg of polyvinylpyrrolidone and 0.45 mg of magnesium stearate; the semipermeable wall comprised 8.36 mg of cellulose triacetate having an acetyl content of 43% and 2.75 mg of hydroxypropylcellulose; and the lamina comprised 60 mg of pseudoephedrine hydrochloride, 4 mg of brompheniramine maleate, 38 mg of polyoxyethylene, 87 mg of hydroxypropylcellulose, 10 mg of hydroxypropylmethylcellulose and 1.0 mg of magnesium stearate. The dosage form had two 15 mil (0.38 mm) passageways, and is indicated for administration twice a day. The dosage form is referred to as a "120/8 B.I.D.", indicating that the compartment comprises 60 mg of pseudoephedrine hydrochloride and 4 mg of brompheniramine maleate, the lamina comprises 60 mg of pseudoephedrine hydrochloride and 4 mg of brompheniramine maleate and the dosage form is indicated for twice a day oral administration.

Other dosage forms were prepared for dispensing pseudoephedrine and brompheniramine. Representative dosage forms contained: (1) a total of 240 mg of pseudoephedrine and 24 mg of brompheniramine with the drug distribution in the dosage form comprising 180 mg of pseudoephedrine and 18 mg of brompheniramine in the compartment and 60 mg of pseudoephedrine and 6 mg of brompheniramine in the lamina; (2) a total of 240 mg of pseudoephedrine and 16 mg of brompheniramine distributed as 180 mg of pseudoephedrine and 10 mg of brompheniramine in the compartment, and 60 mg of pseudoephedrine and 6 mg of brompheniramine in the lamina; and (3) 90 mg of pseudoephedrine and 5 mg of brompheniramine in the compartment, and 30 mg of pseudoephedrine and 3 mg of brompheniramine in the lamina.

A representative example of a 240/16 dosage system, expressed in weight percent (wt %) is as follows: a compartment weighing 260 mg comprising 69% pseudoephedrine hydrochloride, 3.8% brompheniramine maleate, 9.6% sodium chloride, 3% hydroxypropylmethylcellulose, 10% microcrystalline cellulose, 3% poly(vinyl pyrrolidone), 1% magnesium stearate, and 0.5% silicon dioxide, a wall weighing 36.8 mg comprising 75% cellulose triacetate and 25% hydroxypropylcellulose; and, a lamina weighing 84.5 mg comprising 72.7% pseudoephedrine hydrochloride, 7.3% brompheniramine maleate, 7.5% of hydroxypropylmethylcellulose, 8.7% of hydroxypropylcellulose, 3.8% of polyethylene oxide and lubricant to 100%. The dosage form can comprise an additional outermost coat of hydroxypropylmethylcellulose to enhance its taste and to improve its appearance. The dosage form had four 0.5 mm passageways, and delivered its compartment pseudoephedrine hydrochloride in solution at approximately 10 mg/hr, and the brompheniramine maleate delivered in solution at the contracted rate of approximately 0.6 mg/hr.

Another representative example containing a total of 120 mg of pseudoephedrine and 8 mg of brompheniramine comprised the following: a compartment weighing 130 mg consisting essentially of 69.1% pseudoephedrine hydrochloride, 3.8% brompheniramine maleate, 9.6% sodium chloride, 3% hydroxypropylmethylcellulose, 10% microcrystalline cellulose, 3% poly(vinyl pyrrolidone), 1% magnesium stearate, and 0.5% silicon dioxide; a wall weighing 21 mg comprising 75% cellulose triacetate and 25% hydroxypropylcellulose; and a novel lamina forming composition of matter as provided by the invention comprising a lamina weighing 41.6 mg comprising 72.7% pseudoephedrine hydrochloride, 7.3% brompheniramine maleate, 7.5% hydroxypropylmethylcellulose, 8.7% hydroxypropylcellulose, 3.8% polyethylene oxide and other lamina forming ingredients, such as lubricant to 100%. The dosage form had two 0.5 mm passageways and dispensed the pseudoephedrine hydrochloride through the passageways in solution at a rate of about 5 mg/hr and dispensed the bromphniramine maleate in solution through the passageways at a rate of 0.3 mg/hr.

Plasma profiles determined by a computer simulated study using pharmacokinetic data and release rates from dosage forms of the invention indicated a dosage form index of 2.3 for pseudoephedrine and 1.7 for brompheniramine.

In summary, it will be appreciated that the present invention contributes to the art an unobvious dosage form comprising an unobvious lamina composition that possesses practical utility. While the invention has been described and pointed out in detail with reference to operative embodiments thereof, it will be understood that those skilled in the art will appreciate that various changes, modifications, substitutions and omissions can be made without departing from the spirit of the invention. It is intended, therefore, that the invention embraces those equivalents within the scope of the claims which follow.

We claim:

1. An improvement in a dosage form for delivering the beneficial drugs pseudoephedrine and brompheniramine to an environment of use, the dosage form comprising:
    (a) a dosage amount of the beneficial drug pseudoephedrine;
    (b) a dosage amount of the beneficial drug brompheniramine;
    (c) a wall surrounding the pseudoephedrine and the brompheniramine, the wall comprising a cellulose acylate and hydroxypropylcellulose;
    (d) at least one passageway in the wall for delivering the pseudoephedrine and the brompheniramine from the dosage form; and,
    (e) a lamina in laminar arrangement with the exterior of the wall, the lamina comprising pseudoephedrine, brompheniramine, and at least one member selected from the group consisting of hydroxypropylcellulose and hydroxypropylmethylcellulose, the improvement comprising polyethylene oxide present in the lamina for enhancing the lamina's mechanical integrity and its drug releasing pharmacokinetics.

2. The improved dosage form for delivering the beneficial drugs pseudoephedrine and brompheniramine according to claim 1, wherein the cellulose acylate is cellulose triacetate.

3. The improved dosage form for delivering the beneficial drugs pseudoephedrine and brompheniramine according to claim 1, wherein the psuedoephedrine is a pharmaceutically acceptable salt.

4. The improved dosage form for delivering the beneficial drugs pseudoephedrine and brompheniramine according to claim 1, wherein the brompheniramine is a pharmaceutically acceptable salt.

5. An improvement in a dosage form for delivering the beneficial drugs pseudoephedrine and brompheniramine to an environment of use, the dosage form comprising:
    (a) a dosage amount of the beneficial drug pseudoephedrine;
    (b) a dosage amount of the beneficial drug brompheniramine;
    (c) a wall surrounding the pseudoephedrine and the brompheniramine, the wall comprising a cellulose acylate and hydroxypropylcellulose;

(d) at least one passageway in the wall for delivering the pseudoephedrine and the brompheniramine from the dosage form; and, (e) a lamina in laminar arrangement with the exterior surface of the wall, the lamina comprising pseudoephedrine, brompheniramine, and at least one member selected from the group consisting of hydroxypropylcellulose and hydroxypropylmethylcellulose, and wherein the improvement comprises carboxyvinyl polymer present in the lamina for enhancing the lamina's mechanical integrity and pharmacokinetics properties of the dosage form.

6. The improved dosage form for delivering the beneficial drugs pseudoephedrine and brompheniramine to the environment of use according to claim 5, wherein the cellulose acylate is cellulose triacetate.

7. The improved dosage form for delivering the beneficial drugs pseudoephedrine and brompheniramine to the environment of use according to claim 5, wherein the pseudoephedrine is present as its pharmaceutically acceptable salt.

8. The improved dosage form for delivering the beneficial drugs pseudoephedrine and brompheniramine to the environment of use according to claim 5, wherein the brompheniramine is present as its pharmaceutically acceptable salt.

* * * * *